United States Patent
Lindzen et al.

(10) Patent No.: US 9,518,988 B2
(45) Date of Patent: Dec. 13, 2016

(54) ANTIBODIES AND METHODS OF USING SAME FOR TREATING ERBB/ERBB LIGANDS ASSOCIATED DISEASES

(75) Inventors: Moshit Lindzen, Rehovot (IL); Yosef Yarden, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/641,174

(22) PCT Filed: Mar. 22, 2011

(86) PCT No.: PCT/IL2011/000269
§ 371 (c)(1),
(2), (4) Date: Oct. 15, 2012

(87) PCT Pub. No.: WO2011/132182
PCT Pub. Date: Oct. 27, 2011

(65) Prior Publication Data
US 2013/0034565 A1    Feb. 7, 2013

Related U.S. Application Data

(60) Provisional application No. 61/325,330, filed on Apr. 18, 2010.

(51) Int. Cl.
*A61K 39/395* (2006.01)
*G01N 33/574* (2006.01)
(Continued)

(52) U.S. Cl.
CPC ..... *G01N 33/57423* (2013.01); *A61K 31/7068* (2013.01); *A61K 39/3955* (2013.01);
(Continued)

(58) Field of Classification Search
None
See application file for complete search history.

(56) References Cited

U.S. PATENT DOCUMENTS

| | | |
|---|---|---|
| 5,190,858 A | 3/1993 | Sorvillo et al. |
| 8,481,039 B2 * | 7/2013 | Mekada et al. |
| | (Continued) | |

FOREIGN PATENT DOCUMENTS

| | | |
|---|---|---|
| EP | 2070548 | 6/2009 |
| WO | WO 2008/044068 | 4/2008 |
| | (Continued) | |

OTHER PUBLICATIONS

Kang et al., Expression of EGF mRNA and protein in eutopic and ectopic endometrial tissues in patients with endometriosis, Korean J. Obstetrics Gynecol. 52(2):237-244, Feb. 2009.*

(Continued)

*Primary Examiner* — Claire Kaufman

(57) ABSTRACT

A method of selecting a target for treatment of a hyperproliferative disease in a subject in need thereof is disclosed. The method comprising analyzing an amount and/or activity of at least one ErbB ligand in a biological sample from the subject, wherein an ErbB ligand which shows an up-regulated amount and/or activity compared to a non-hyperproliferative cell or tissue above a predetermined level is selected as a target for treatment of the hyperproliferative disease. Methods of treating hyperproliferative diseases, monoclonal antibodies and pharmaceutical compositions are also disclosed.

6 Claims, 6 Drawing Sheets

(51) Int. Cl.
  A61K 31/7068    (2006.01)
  C07K 16/22      (2006.01)
  G01N 33/50      (2006.01)
  A61K 39/00      (2006.01)
(52) U.S. Cl.
  CPC .......... *C07K 16/22* (2013.01); *G01N 33/5011* (2013.01); *G01N 33/57438* (2013.01); *G01N 33/57492* (2013.01); *A61K 2039/505* (2013.01); *A61K 2039/507* (2013.01); *C07K 2317/73* (2013.01); *C07K 2317/76* (2013.01); *G01N 2500/00* (2013.01)

(56) References Cited

U.S. PATENT DOCUMENTS

2002/0193301 A1   12/2002   Twardzik et al.
2006/0193854 A1    8/2006   Adams et al.

FOREIGN PATENT DOCUMENTS

| WO | WO 2008/047723 | 4/2008  |
| WO | WO 2009/126310 | 10/2009 |
| WO | WO 2010/029534 | 3/2010  |
| WO | WO 2011/132182 | 10/2011 |

OTHER PUBLICATIONS

Wong et al., The role of epidermal growth factor and its receptors in mammalian CNS, Cytokine Growth Factor Rev. 15:147-156, 2004.*

NCIthesauras, Acquired Immunodeficiency Syndrome (Code C2851), No. 26, 2013 [online], [retrieved on Feb. 4, 2014]. Retrieved from the Internet <URL:http://ncit.nci.nih.gov/ncitbrowser/pages/home.jsf>.*

Larbouret et al., In vivo therapeutic synergism of anti-epidermal growth factor receptor and anti-HER2 monoclonal antibodies against pancreatic carcinomas, Clin. Cancer Res. 13:3356-3362, 2007.*

Sarup et al., Human epidermal growth factor receptor (HER-1:HER-3) Fc-mediated heterodimer has broad antiproliferative activity in vitro and in human tumor xenografts, Med. Cancer Ther. 7(10):3223-3236, Oct. 2008.*

Révillon et al., ErbB/HER ligands in human breast cancer, and relationships with their respective receptors, the bio-pathological features and prognosis, Annals Oncol. 19:73-80, 2008.*

Stromberg et al., Transforming growth factor-alpha acts as an autogrin growth factor in ovarian carcinoma cell lines, Cancer Res. 52:341-347, Jan. 15, 1992.*

NCI Thesauras, Cure (Code C62220) [online], Retrieved from <URL: http://ncit.nci.nih.gov/ncitbrowser/ConceptReport.jsp?dictionary=NCI_Thesaurus&version=14.06e&code=C62220&ns=NCI_Thesaurus&key=1804076014&b=1&n=null> [retrieved on Aug. 14, 2014] 2014.*

Penzel et al., The epidermal growth factor receptor family as a central element for cellular signal transduction and diversification, Endocrine-Related Cancer, 8:11-31, 2001.*

Shin et al., The chemical synthesis and binding affinity of the EGF recepotr of the EGF-like domain of heparine-binding EGF-like growth factor (HB-EGF), J. Pep. Sci. 9:244-250, 2003.*

Chen et al., Enhancement and destruction of antibody function by somatic mutation: unequal occurrence is controlled by V gene combinatorial associations, EMBO J., 14 (12): 2784-2794, 1995.*

International Search Report and the Written Opinion Dated Jul. 1, 2011 From the International Searching Authority Re. Application No. PCT/IL2011/000269.

Bacus et al. "Targeted Use of Combination of ErbB Targeted Therapy", Breast Cancer Research and Treatment, XP009148207, 88(Suppl.1): S181-S182, #4099, Jan. 1, 2004.

Lindzen et al. "Tailored Cancer Immunotherapy Using Combinations of Chemotherapy and a Mixture of Antibodies Against EGF-Receptor Ligands", Proc. Natl. Acad. Sci. USA, XP002637066, 107(28): 12559-12563, Jul. 13, 2010.

International Preliminary Report on Patentability Dated Nov. 1, 2012 From the International Bureau of WIPO Re. Application No. PCT/IL2011/000269.

Patent Examination Report Dated Apr. 16, 2014 From the Australian Government, IP Australia Re. Application No. 2011243958.

Notice of Reason for Rejection Dated Jul. 11, 2014 From the Japanese Patent Office Re. Application No. 2013-505597 and Its Translation Into English.

Castillo et al. "Amphiregulin Contributes to the Transformed Phenotype of Human Hepatocellular Carcinoma Cells", Cancer Research, 66(12): 6129-6138, Jun. 15, 2006.

Miyamoto et al. "Heparin-Binding EGF-Like Growth Factor Is a Promising Target for Ovarian Cancer Therapy", Cancer Research, 64(16): 5720-5727, Aug. 15, 2004.

Office Action Dated Jul. 30, 2014 From the State Intellectual Property Office of The People's Republic of China Re. Application No. 201180030067.4 and Its Translation Into English.

Patent Examination Report Dated Sep. 18, 2014 From the Australian Government, IP Australia Re. Application No. 2011243958.

Search Report Dated Jul. 30, 2014 From the State Intellectual Property Office of The People's Republic of China Re. Application No. 201180030067.4 and Its Translation Into English.

Das et al. "Heparin-Binding EGF-Like Growth Factor Gene Is Induced in the Mouse Uterus Temporally by the Blastocyst Solely at the Site of Its Apposition: A Possible Ligand for Interaction With Blastocyst EGF-Receptor in Implantation", Development, 120: 1071-1083, Dec. 31, 1994. P.1073, Right Col., Para 2.

Office Action Dated Apr. 3, 2015 From the State Intellectual Property Office of The People's Republic of China Re. Application No. 201180030067.4 and Its Translation Into English.

Request for Examination Dated Feb. 23, 2015 From the Rospatent, Federal Government Institution, Federal Institute of Industrial Property of the Federal Service of Intellectual Property, Patents and Trademarks of the Russian Federation Re. Application No. 2012148398 and Its Translation Into English.

Nakamura et al. "Apoptosis in Human Hepatoma Cell Line Induced by 4,5-Didehydro Geranylgeranoic Acid (Acyclic Retinoid) Via Down-Regulation of Transfoiiuing Growth Factor-Alpha", Biochemical and Biophysical Research Communications, 219(1): 100-104, Feb. 6, 1996. Abstract.

Office Action and Search Report Dated Sep. 6, 2015 From the State Intellectual Property Office of The People's Republic of China Re. Application No. 201180030067.4 and Its Translation Into English.

Crijns et al. "Molecular Prognostic Markers in Ovarian Cancer: Toward Patient-Tailored Therapy", International Journal of Gynecological Cancer, 16(Supp1.1): 152-165, Jan.-Feb. 2006.

Office Action Dated Jun. 14, 2015 From the Israel Patent Office Re. Application No. 222447 and Its Translation Into English.

Examination Report Dated Jul. 29, 2015 From the Instituto Mexicano de la Propiedad Industrial Re. Application No. MX/a/2012/012075 and Its Translation Into English.

\* cited by examiner

ANTIBODIES AND METHODS OF USING SAME FOR TREATING ERBB/ERBB LIGANDS ASSOCIATED DISEASES

RELATED APPLICATIONS

This application is a National Phase of PCT Patent Application No. PCT/IL2011/000269 having International filing date of Mar. 22, 2011, which claims the benefit of priority under 35 USC §119(e) of U.S. Provisional Patent Application No. 61/325,330 filed on Apr. 18, 2010. The contents of the above applications are all incorporated by reference as if fully set forth herein in their entirety.

GOVERNMENT INTERESTS

Statement Regarding Federally Sponsored Research or Development

This invention was made with government support under CA 72981 awarded by the NIH. The government has certain rights in the invention.

FIELD AND BACKGROUND OF THE INVENTION

The present invention relates to methods of selecting agents for the treatment of hyperproliferative diseases such as cancer and to combinations of agents for the treatment of same.

The ErbB family of tyrosine kinase receptors and ligands which bind same play an important role in embryonic development, as well as in tissue remodeling throughout adulthood. The signaling cascade initiates with ligand binding, which leads to receptor dimerization and phosphorylation, and results in various cellular processes, including proliferation, differentiation, migration and survival.

There are four closely related ErbB receptors: ErbB-1 [epidermal growth factor receptor (EGFR)] which binds epidermal growth factor (EGF), transforming growth factor α (TGFα), heparin-binding EGF-like growth factor (HB-EGF), amphiregulin (AR), betacellulin (BTC), epiregulin (EPR) and epigen; ErbB-3 and ErbB-4 which bind neuregulin growth factors; and ErbB-2 (HER2) which currently has no known ligands.

All ErbB family ligands share a 50-60 amino acid-long sequence containing six cysteines in a conserved spacing and context, collectively called the epidermal growth factor (EGF) motif. This motif is the central structural and functional feature responsible for receptor recognition. The growth factors are synthesized as type I transmembrane proteins and ectodomain shedding occurs (via proteolytic processing) which leads to the release of the soluble growth factor (comprising an EGF-like domain). The soluble ligand may in turn bind and activate receptors on distant cells, neighboring cells, or on the cells of its origin. Some membrane-anchored ligands can also activate EGFR on membranes of adjacent cells, a mechanism which may induce different biological outcomes than soluble ligands.

The ErbB proteins have been described in involvement of several pathologies, including psoriasis, arthrosclerosis, as well as in several types of human cancer. For instance, many tumors of epithelial origins express an increased level of ErbB-1 on their cell surface [Ullrich, A. et al. (1984) Nature 309, 418-425]. Tumors with increased ErbB receptor expression often display increased production of TGFα, or other ErbB ligands, allowing receptor activation by an autocrine loop.

Clinical studies indicate that overexpression of one or more ErbB ligands correlates with decreased patient survival. For example, widespread expression of TGFα within primary colorectal tumor specimens is associated with a greater than 50-fold increased risk of developing liver metastases [Barozzi, C. et al. (2002) Cancer 94, 647-657]. In bladder cancer, the elevated expression of a number of ErbB ligands (AR, HB-EGF, TGFα and particularly EPR) is linked to decreased patient survival [Thogersen, V. B. et al. (2001) Cancer Res 61, 6227-6233]. In addition, elevated TGFα expression in metastatic disease is associated with poorer patient outcome [De Jong, K. P. et al (1998) Hepatology 28, 971-979] and increased expression of TGFα in head and neck tumors is correlated with decreased patient survival [Grandis, J. R. et al. (1998) J Cell Biochem 69, 55-62]. Moreover, tumor cell expression of some ligands, notably TGFα, AR and HB-EGF, is associated with resistance to chemotherapeutics [Eckstein, N. et al. (2008) J Biol Chem 283, 739-750; Wang, F. et al. (2007) Oncogene 26, 2006-2016].

Emerging data indicates that the expression of specific ErbB ligands in certain tumors is differently associated with prognosis. EGF expression in breast tumor samples is associated with more favorable prognosis whereas TGFα expression is associated with a more aggressive tumor [Revillion, F. et al. (2008) Int J Biol Markers 23, 10-17]. Likewise, microarray analyses revealed that early hyperplastic precursors of breast cancer display increased AR transcription and decreased EGF transcription relative to normal breast tissues [Lee, S. et al. (2007) Am J Pathol 171, 252-262]. In patients with non-small cell lung carcinoma (NSCLC), TGFα and AR serum concentration correlate with tumor aggressiveness [Lemos-Gonzalez, Y. et al. (2007) Br J Cancer 96, 1569-1578]. Taken together, this data suggests that TGFα and AR are associated with EGFR-associated tumor cell aggressiveness and chemoresistance, while EGF may in fact antagonize stimulation of pathogenic signaling by TGFα and AR [Wilson, K. J. et al. (2009) Pharmacol Ther 122, 1-8].

Currently approved drugs for the treatment of ErbB associated cancers include monoclonal antibodies directed at ErbB-1 (EGFR, e.g. erbitux/cetuximab) or at HER2 (ErbB-2, e.g. herceptin/trastuzumab), or small-molecule tyrosine kinase inhibitors (TKI, e.g. tarceva/erlotinib) [Britten, C. D. (2004) Mol Cancer Ther 3, 1335-1342; Weiner, L. M., and Borghaei, H. (2006) Hum Antibodies 15, 103-111]. Acquired resistance to monoclonal antibodies (such as trastuzumab) or tyrosine kinase inhibitors (such as gefitinib) is often associated with up-regulation of ErbB receptors or ligands, for example, human breast cancer cells selected in vivo for resistance to trastuzumab remarkably overexpressed EGFR and the ErbB ligands TGFα, HB-EGF and NRG1 [Ritter, C. A. et al. (2007) Clin Cancer Res 13, 4909-4919]. Likewise, EGFR- and HER2-targeting monoclonal antibodies increase the anti-tumor effects of docetaxel by blocking functional receptors and drug evasion mechanisms [Bijman, M. N. et al. (2009) Anticancer Drugs 20, 450-460; Freeman, D. J. et al. (2009). Mol Cancer Ther 8, 1536-1546].

Additionally, alternative strategies that directly target ligands have been proposed. One such strategy is monoclonal antibodies specific for individual ligands. For example, bevacizmab is a humanized monoclonal antibody that binds vascular endothelial growth factor-A (VEGF-A) [Hurwitz, H., et al. (2004) N Engl J Med 350, 2335-2342; Shih, T., and Lindley, C. (2006) Clin Ther 28, 1779-1802]. Another strategy makes use of "ligand-traps", soluble ligand-binding domains of specific receptors. An example for such a ligand-trap is etanercept, a fusion protein comprising the ligand-binding domain of the TNF-α receptor fused to the human immunoglobulin G (IgG) Fc region, which is used for the treatment of rheumatoid arthritis [Mohler, K. M., et al. (1993) J Immunol 151, 1548-1561]. Another alternative is the inhibition of the shedding agents, members of the disintegrin and metalloproteinase (ADAM) family, which are thought to mediate the shedding of EGFR ligands, an event critical for the production of functional EGFR ligands [Kataoka, H. (2009) J Dermatol Sci 56, 148-153; Kenny, P. A., and Bissell, M. J. (2007) J Clin Invest 117, 337-345; Merchant, N. B., et al. (2008) Clin Cancer Res 14, 1182-1191].

Additional monoclonal antibodies targeting ErbB ligands have been described in the art. For example, PCT Publication No. WO 2009/026705 describes monoclonal antibodies targeting TGFα for the treatment of osteoarthritis.

U.S. Pat. No. 7,501,122 describes treatment with anti-ErbB2 antibody combinations. Specifically, U.S. Pat. No. 7,501,122 teaches treating cancer (e.g. breast cancer, colon cancer) using humanized anti-ErbB2 antibodies. The antibodies described by the teachings of the invention may be administered together or separately to blocks ligand activation of an ErbB receptor in cancers which overexpress epidermal growth factor receptor (EGFR) or EGFR ligands (e.g. EGF, TGF-α or HB-EGF) and thereby inhibit the growth of cancer cells.

U.S. Pat. No. 7,485,302 describes methods for treating cancer using anti-ErbB2 antibodies and chemotherapeutic agents. Specifically, U.S. Pat. No. 7,485,302 teaches the use a chemotherapeutic agent along with anti-ErbB2 antibodies for the treatment of cancer (e.g. breast cancer, lung cancer) which overexpresses epidermal growth factor receptor (EGFR) or ligands thereof (e.g. TGFα).

SUMMARY OF THE INVENTION

According to an aspect of some embodiments of the present invention there is provided a method of selecting a target for treatment of a hyperproliferative disease in a subject in need thereof, the method comprising analyzing an amount and/or activity of at least one ErbB ligand in a biological sample from the subject, wherein an ErbB ligand which shows an up-regulated amount and/or activity compared to a non-hyperproliferative cell or tissue above a predetermined level is selected as a target for treatment of the hyperproliferative disease.

According to an aspect of some embodiments of the present invention there is provided a method of treating a hyperproliferative disease in a subject in need thereof, the method comprising: (a) selecting a target for treatment of a hyperproliferative disease; and (b) administering a therapeutically effective amount of an agent which down-regulates an amount and/or activity of the target to the subject, thereby treating the hyperproliferative disease in the subject.

According to an aspect of some embodiments of the present invention there is provided a method of treating a hyperproliferative disease in a subject in need thereof, the method comprising: (a) administering a therapeutically effective amount of an agent which down-regulates an amount and/or activity of a first ErbB ligand; and (b) administering a therapeutically effective amount of an agent which down-regulates an amount and/or activity of a second ErbB ligand, the first and the second ErbB ligand being non-identical, thereby treating the hyperproliferative disease in the subject.

According to an aspect of some embodiments of the present invention there is provided a pharmaceutical composition comprising a pharmaceutically acceptable carrier and a first active agent which down-regulate an amount and/or activity of a first ErbB ligand and a second active agent which down-regulate an amount and/or activity of a second ErbB ligand, the first and the second ErbB ligand being non-identical.

According to an aspect of some embodiments of the present invention there is provided an article of manufacture comprising a packaging material and a first agent which down-regulates an amount and/or activity of a first ErbB ligand and a second agent which down-regulates an amount and/or activity of a second ErbB ligand, the first and the second ErbB ligand being non-identical, the article of manufacture being identified in print in or on the packaging material for treatment of a hyperproliferative disease.

According to an aspect of some embodiments of the present invention there is provided a monoclonal antibody or fragment thereof, capable of specifically binding to at least one epitope of an EGF-like domain of TGFα as described by deposit number CNCM I-4292 (Clone No. 551.6.103), deposited at the Collection Nationale De Cultures De Microorganismes (CNCM).

According to an aspect of some embodiments of the present invention there is provided a monoclonal antibody or fragment thereof, capable of specifically binding to at least one epitope of an EGF-like domain of HB-EGF as described by deposit number CNCM I-4291 (Clone No. 898.47), deposited at the Collection Nationale De Cultures De Microorganismes (CNCM).

According to some embodiments of the invention, the agent comprises an antibody or fragment thereof which specifically binds the target.

According to some embodiments of the invention, the agent comprises a siRNA which specifically binds the target.

According to some embodiments of the invention, administering comprises administering at least two agents, each of the two agents specifically binding to a non-identical target.

According to some embodiments of the invention, the agent comprises an antibody or fragment thereof which specifically binds the first ErbB ligand and/or the second ErbB ligand.

According to some embodiments of the invention, the agent comprises a siRNA which specifically binds the first ErbB ligand and/or the second ErbB ligand.

According to some embodiments of the invention, the method further comprises administering to the subject a chemotherapeutic agent.

According to some embodiments of the invention, the hyperproliferative disease is cancer.

According to some embodiments of the invention, the cancer is a pancreatic cancer.

According to some embodiments of the invention, the cancer is a lung cancer.

According to some embodiments of the invention, the biological sample comprises cancerous cells.

According to some embodiments of the invention, analyzing is effected by ELISA.

According to some embodiments of the invention, the ErbB ligand is selected from the group consisting of epidermal growth factor (EGF), transforming growth factor-α (TGFα), heparin-binding EGF-like growth factor (HB- EGF), amphiregulin (AR), betacellulin (BTC), epiregulin (EPR), epigen and neuregulin growth factor.

According to some embodiments of the invention, the first ErbB ligand comprises transforming growth factor α (TGFα).

According to some embodiments of the invention, the second ErbB ligand comprises heparin-binding EGF-like growth factor (HB-EGF).

According to some embodiments of the invention, the pharmaceutical composition further comprises a chemotherapeutic agent.

According to some embodiments of the invention, the article of manufacture further comprises a chemotherapeutic agent.

According to some embodiments of the invention, the first agent and the second agent are formulated in separate pharmaceutical compositions.

According to some embodiments of the invention, the first agent and the second agent are formulated in a single pharmaceutical composition.

According to some embodiments of the invention, the monoclonal antibody or fragment thereof comprises a detectable moiety.

According to some embodiments of the invention, the monoclonal antibody or fragment thereof comprises a cytotoxic agent attached thereto.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A shows a scheme of the general chimeric protein, including a thioredoxin (TRX) domain, a histidine box (6×His), a flanking Factor Xa cleavage site and a carboxyl-terminal EGF-like domain. Residue numbers are indicated. FIG. 1B shows coomassie blue staining of an acrylamide gel showing purified TGFα and HB-EGF prepared using bacterial expression and purified on a NiNTA column. Molecular weight markers are indicated in kilodaltons. FIG. 1C shows the biological activity of the purified proteins as was verified by testing their ability to induce EGFR phosphorylation on tyrosine residues. Cells were seeded in a 24-well plate, washed and incubated with increasing concentrations of the purified fusion proteins (TRX-TGFα: 2, 20, 200 ng/ml; TRX-HB-EGF: 3, 30, 300 ng/ml). EGF (10 ng/ml) was used as a positive control. After 10 minute incubation, the cells were lysed, and cleared extracts were immunoblotted (IB) with an anti-phosphotyrosine (P-Tyr) antibody. FIG. 1D shows a scheme presenting the domain structure of a generic GPI (glycosyl phosphatidylinositol) fusion protein comprising the ErbB-2's signal peptide (SP), the EGF-like domain of TGFα (or HB-EGF), an HA peptide tag, and a GPI lipid anchor that enables anchoring in the plasma membrane. Residue numbers refer to TGFα. Cysteine residues of the EGF-like domain are highlighted. FIG. 1E shows TGFα-induced phosphorylation of EGFR as was tested in the presence of increased amounts of antisera from an immunized mouse. Cells were seeded in a 24-well plate, washed and incubated with or without TGFα (5 ng/ml), and with increasing volumes of an anti-serum from TGFα-immunized mice (0.2, 2, 4, 6, 8 and 10 μl of serum diluted in 120 μl total; control: 10 μl serum from a naive animal). An anti-phosphotyrosine mAb was used to detect phosphorylated EGFR.

FIG. 2A shows antigen specificity. 96-well plates were coated with the indicated ligands (0.1 ng/ml), then incubated with an anti-TGFα mAb551 (gray) or with saline (blank) for 2 hours. Thereafter, wells were incubated for 1 hour with an anti-mouse antibody conjugated to HRP, followed by a 30 minute incubation with ATBS. Signals were determined using an ELISA Reader (set at 420 nm). FIG. 2B shows immunoprecipitation of the anti-TGFα mAb with a commercial preparation of TGFα. Anti-TGFα mAb551 antibody was used to immunopercipitate TGFα (50 ng; Sigma) using beads conjugated to anti-mouse Fc antibodies. Immune complexes were blotted with mAb551. A molecular weight marker (7 Kilodalton) is indicated. FIG. 2C shows the ability of mAb-551 to specifically inhibit TGFα-induced EGFR phosphorylation. Cells were seeded in a 24-well plate, and after 10 hours of incubation they were washed and incubated for 10 min with or without the indicated ligands and increasing concentrations of an anti-TGFα mAb (15, 80 and 160 mg/ml). Thereafter, cells were lysed and cleared extracts immonublotted (IB) with an anti-phosphotyrosine mAb or with an anti-EGFR mAb, as indicated.

FIG. 3A shows antigen specificity. 96-well plates were coated with the indicated ligands (0.1 ng/ml), then incubated with anti-HB-EGF mAb898 (white), anti-HB-EGF mAb878 (grey) or anti-HB-EGF mAb384 (black) for 2 hours. Thereafter, wells were incubated for 1 hour with an anti-mouse antibody conjugated to HRP, followed by 30 minute incubation with ATBS. Signals were determined using an ELISA Reader (set at 420 nm). FIG. 3B shows immunoprecipitation of the commercial preparation of HB-EGF using different anti-HB-EGF mAbs. The indicated mAbs to HB-EGF were used to immunopercipitate (IP) HB-EGF (Sigma; St. Louis, Mo.) using beads conjugated to anti-mouse Fc antibodies. Immune complexes were immunoblotted with mAb327 to HB-EGF. A molecular weight marker is indicated. FIG. 3C depicts the ability of HB-EGF mAbs to specifically inhibit HB-EGF-induced EGFR phosphorylation. Sparse monolayers of HeLa or T47D cells were washed and incubated for 10 min with HB-EGF (3 ng/ml) and different anti HB-EGF mAbs (384, 878, 898). Thereafter, cells were lysed and cleared extracts immunoblotted with an anti-phosphotyrosine mAb, an anti-EGFR mAb (HeLa) or an anti ErbB-3 mAb (T47D).

FIG. 4A shows reduced in vitro cell growth of pancreatic cancer cells treated with the mAbs of the present invention. BxPC3 cells ($2\times10^4$) were seeded in a 96-well plate and allowed to adhere overnight, prior to the addition of anti-TGFα or anti-HB-EGF mAbs (each at 30 μg/ml), or a mixture of both mAbs (each at 15 μg/ml). Cell proliferation was determined in hexaplicates after 96 hours using the MTT method. Averages±S.D. are shown. The experiment was repeated twice. FIG. 4B shows reduced in vivo cell growth of pancreatic cancer cells in mice treated with the mAbs of the present invention. Female nude mice (6 week old) were inoculated subcutaneously with $2\times10^6$ BxPC3 cells. Once tumors became palpable (5-7 days) mice were randomized into groups and intraperitoneally injected with an anti-TGFα or anti-HB-EGF mAb (each at 125 μg per injection), or with a combination of both mAbs (each at 125 μg per injection). Mice were treated with mAbs on days 9, 16, 20, 23, 26, 30, 33, 37, 40 and 44. The control group included 12 mice and each treatment group included 8 mice. Of note, no differences in the body weights of the mice were observed (not shown).

FIG. 5A shows reduced in vitro cell growth of pancreatic cancer cells treated with the mAbs of the present invention along with chemotherapy. BxPC3 cells ($2\times10^4$) were treated as described in FIG. 4A (above), with the exception that gemcitabine (50 mg/ml) was used, either alone or in combination with the mixture of anti-TGFα and anti-HB-EGF mAbs (each at 15 μg/ml). The experiment was repeated twice. FIG. 5B shows reduced in vivo cell growth of pancreatic cancer cells in mice treated with the mAbs of the present invention along with chemotherapy. Female nude mice (6 week old) were inoculated subcutaneously with $2\times10^6$ BxPC3 cells. Once tumors became palpable (5-7 days) mice were randomized into groups. The first group was intraperitoneally injected with a mixture of mAbs specific for TGFα and HB-EGF (each at 250 μg per injection; depicted by white arrows). A second group (11 mice) was treated on days 16 and 21 with gemcitabine (intraperitoneal injection, 150 mg/kg body weight; depicted by black arrows), and a third group (6 mice) was treated with a combination of gemcitabine and mAbs. The control group (11 mice) was treated with saline. Averages±S.D. of tumor volume are shown. Of note, body weight monitoring detected no consistent trends and differences other than a slow gain of weight (data not shown).

DESCRIPTION OF SPECIFIC EMBODIMENTS OF THE INVENTION

The present invention relates to methods of selecting agents for the treatment of hyperproliferative diseases such as cancer and to combinations of agents for the treatment of same.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

ErbB proteins are known to be involved in several pathologies, including psoriasis, arthrosclerosis, as well as in several types of human cancer. Clinical studies indicate that over-expression of one or more ErbB ligand correlates with decreased patient survival.

The present inventors now propose that therapies for the treatment of cancer can be selected and individually tailored according to a particular patient's needs based on an expression profile of ErbB in biological samples derived therefrom. Moreover, the present inventors have shown that combination treatment with two monoclonal antibodies targeting ErbB ligands (e.g. TGFα and HB-EGF) both of which are specifically up-regulated in a particular tumor, significantly reduces growth of that tumor and is advantageous in cancer treatment.

Figure 2A:
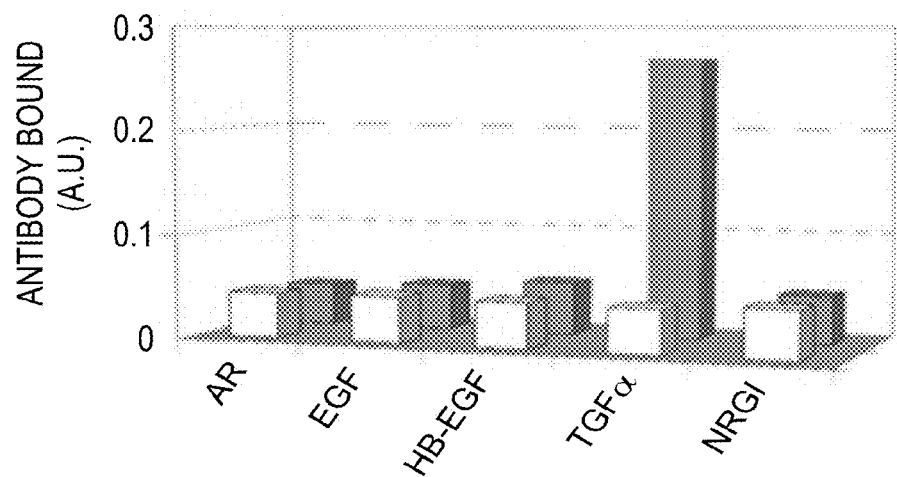
FIGS. 2A-C depict antigen specificity and functional tests of the anti TGFα mAb.
Figure 3A:
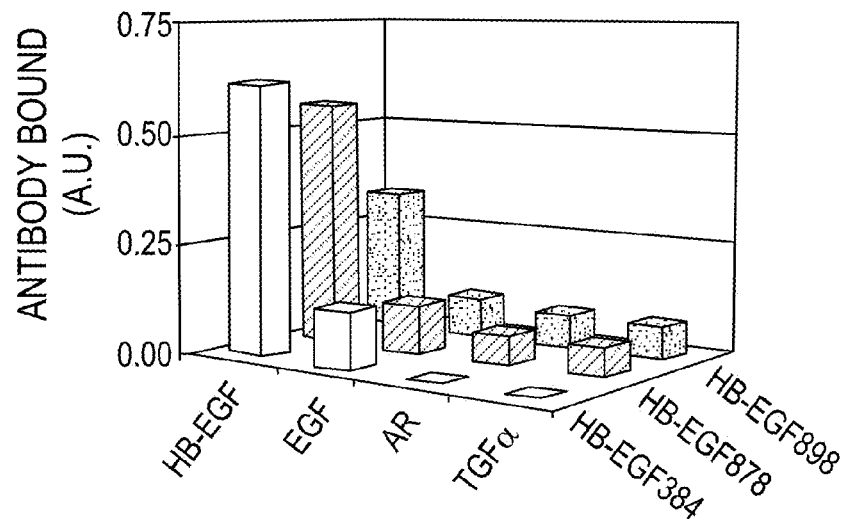
FIGS. 3A-C depicts functional tests of anti HB-EGF mAbs.
Figure 4A:
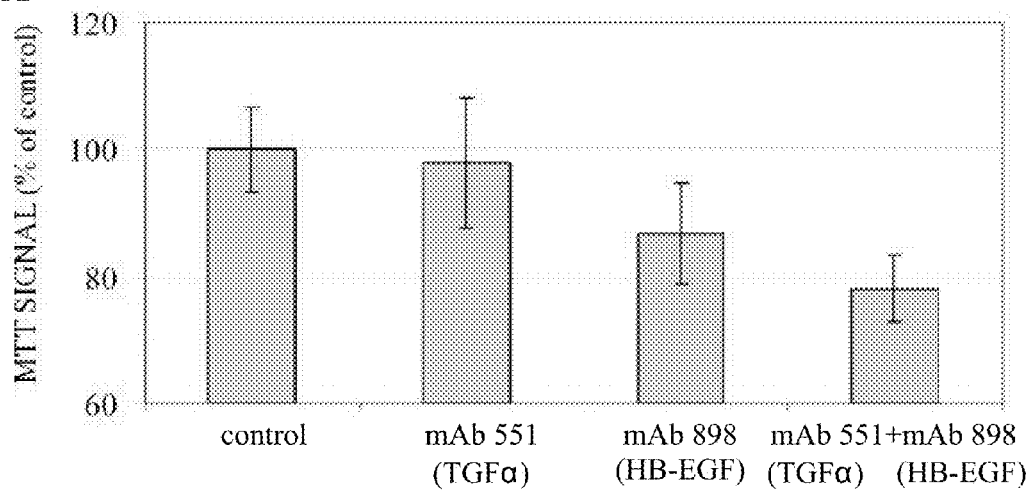
FIGS. 4A-B depict effective inhibition of proliferation and tumorigenicity (in vitro and in vivo) of human pancreatic cancer cells by a combination of anti-TGFα and anti- HB-EGF mAbs.
Figure 4B:
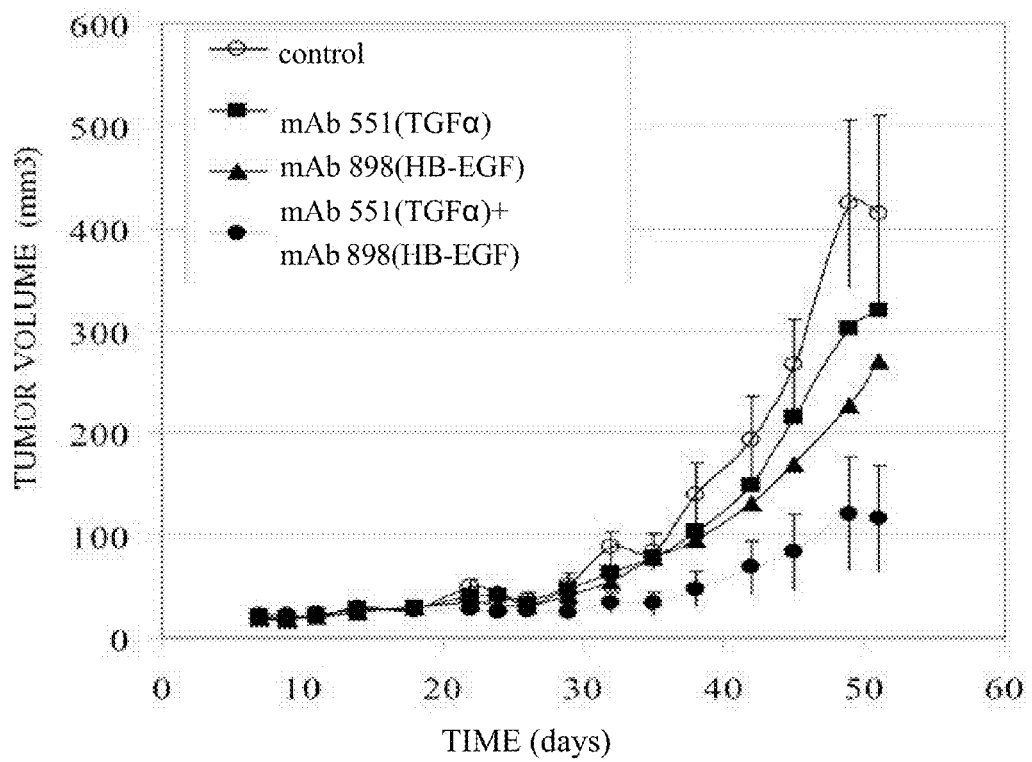

Specifically, the present inventors have shown that pancreatic tumors sustain several autocrine loops involving EGFR and ErbB ligands, namely TGFα, HB-EGF and AR (see Table 1, hereinbelow). Inventors generated specific monoclonal antibodies targeting TGFα (mAb 551, Example 3 hereinbelow) and HB-EGF (mAb 898, mAb 878 and mAb 384, Example 4 hereinbelow) and showed that these antibodies are specific to their target ligand (FIGS. 2A and 3A, respectively). Furthermore, the use of these mAbs alone or in combination significantly reduced tumor growth in vitro (FIG. 4A) and in vivo (FIG. 4B). Importantly, adding these mAbs to conventional chemotherapeutic drugs, like gemcitabine, increased efficiency of treatment (FIGS. 5A-B) probably by sensitizing tumors to cytotoxicity and delaying the onset of chemoresistance. Taken together the present teachings portray a therapeutic value for monoclonal antibodies targeting ErbB ligands and suggest the use of same for the treatment of tumors.

Thus, according to one aspect of the present invention there is provided a method of treating a hyperproliferative disease in a subject in need thereof, the method comprising: (a) analyzing an amount and/or activity of at least one ErbB ligand in a biological sample from the subject, wherein an ErbB ligand which shows an up-regulated amount and/or activity compared to a non-hyperproliferative cell or tissue above a predetermined level is selected as a target for treatment of a hyperproliferative disease; and (b) administering a therapeutically effective amount of an agent which down-regulates an amount and/or activity of the target to the subject, thereby treating the hyperproliferative disease in the subject.

The term "treating" as used herein refers to preventing onset of the disease, alleviating, attenuating, palliating or eliminating the symptoms of a disease, slowing, reversing or arresting the progression of the disease, or curing the disease.

As used herein the phrase "hyperproliferative disease" refers to any disease which is characterized by a rapid and/or uncontrolled cell division and which depends on ErbB ligand (activity and/or expression) for onset and/or progression. Such a disease may be cancerous or benign.

Hyperproliferative diseases may include, but are not limited to, cancer; skin diseases such as psoriasis, actinic keratosis, seborrheic keratosis, lamellar ichthyosis, toxic eczema, allergic eczema, atopic dermatitis and Bowen's Disease; myelodysplastic disorders; cervical carcinoma-in-situ; familial intestinal polyposes such as Gardner syndrome; oral leukoplakias; histiocytoses; keloids; hemangiomas; inflammatory arthritis; hyperkeratoses and papulosquamous eruptions including arthritis. Also included are viral induced hyperproliferative diseases such as warts and EBV induced disease (i.e., infectious mononucleosis), scar formation, blood vessel proliferative disorders such as restenosis, atherosclerosis, in-stent stenosis, vascular graft restenosis, etc.; fibrotic disorders; glomerular nephritis; macular degenerative disorders; benign growth disorders such as prostate enlargement and lipomas; autoimmune disorders; Cardiac dysrhythmias; Endometriosis, uterine fibroid (Uterine leiomyomata) menorrhagia, cervical erosion, cervical polyp; and defects or disorders of intervertebral discs.

According to a specific embodiment, the hyperproliferative disease is cancer.

As used herein the term "cancer" refers to a cancerous disease which depends on ErbB ligand (activity and/or expression) for onset and/or progression. Cancer cells may be associated with phenotypes such uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally within an animal, or circulate in the blood stream as independent cells, for example, leukemic cells. It will be appreciated that the term cancer as used herein encompasses all types of cancers, at any stage and in any form.

Types of tumoral diseases amenable to treatment via the method of the present invention include benign tumors, warts, polyps, precancers, and malignant tumors/cancer.

Specific examples of tumoral diseases which can be treated using the methods of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial non-chromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the present invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to a specific embodiment of this aspect of the present invention, the cancer is pancreatic cancer or lung cancer.

As used herein, the phrase "pancreatic cancer" refers to a malignant neoplasm of the pancreas, including but not limited to, adenocarcinomas, adenosquamous carcinomas, signet ring cell carcinomas, hepatoid carcinomas, colloid carcinomas, undifferentiated carcinomas, undifferentiated carcinomas with osteoclast-like giant cells and islet cell carcinomas.

As used herein, the phrase "lung cancer" refers to any uncontrolled cell growth in tissues of the lung, including but not limited to, small cell lung carcinoma, combined small cell carcinoma, non-small cell lung carcinoma, sarcomatoid carcinoma, salivary gland tumors, carcinoid tumor, adenosquamous carcinoma, pleuropulmonary blastoma and carcinoid tumor.

As used herein, the phrase "subject in need thereof" refers to a subject which has a hyperproliferative disease (e.g. cancer), or which is susceptible to having a hyperproliferative disease. The subject may be a mammal, e.g. a human. For example, if the disease being treated is pancreatic cancer, the subject is typically one having being diagnosed with pancreatic cancer, with or without metastasis, at any stage of the disease.

The term "ErbB ligand" as used herein, refers to the epidermal growth factor (EGF) gene product (i.e., protein or mRNA) such as set forth in GenBank Accession Nos. NM_001963 or NP_001954; the transforming growth factor α (TGFα) gene product (i.e., protein or mRNA) such as set forth in GenBank Accession Nos. NM_003236 or NP_003227; the heparin-binding EGF-like growth factor (HB-EGF) gene product (i.e., protein or mRNA) such as set forth in GenBank Accession Nos. NM_001945 or NP_001936; the amphiregulin (AR) gene product (i.e., protein or mRNA) such as set forth in GenBank Accession Nos. NM_001657 or NP_001648; the betacellulin (BTC) gene product (i.e., protein or mRNA) such as set forth in GenBank Accession Nos. NM_001729 or NP_001720; the epiregulin (EPR) gene product (i.e., protein or mRNA) such as set forth in GenBank Accession Nos. NM_001432 or NP_001423; the epigen gene product (i.e., protein or mRNA) such as set forth in GenBank Accession Nos. NM_001013442 or NP_001013460; and the neuregulin gene products (i.e., protein or mRNA) including Neuregulin 1 (NRG1) such as set forth in GenBank Accession Nos. NM_004495 or NP_004486, Neuregulin 2 (NRG2) such as set forth in GenBank Accession Nos. NM_013981 or NP_053584, Neuregulin 3 (NRG3) such as set forth in GenBank Accession Nos. NM_001010848 or NP_001010848, and Neuregulin 4 (NRG4) such as set forth in GenBank Accession Nos. NM_138573 or NP_612640.

As is shown in Table 1, hereinbelow, and is described in Example 1 of the Examples section which follows, the present inventors have uncovered that cancer cells secrete up-regulated levels of ErbB ligands and in distinct combinations of same.

As used herein, the amount of an ErbB ligand refers to an intracellular, cell membranal, cell surface and/or cell-proximal amount of an ErbB ligand (e.g. ErbB ligand mRNA, ErbB ligand polypeptide). The activity of the ErbB ligand, as used herein, refers to binding of same to its appropriate ErbB receptor (e.g. binding of EGF, TGFα or HB-EGF to an ErbB-1 receptor) and activating same (e.g. activating intracellular signal transduction pathways).

In order to select a target for treatment of the hyperproliferative disease, a biological sample is first obtained from the subject and analyzed for ErbB ligand amount and/or activity.

According to one embodiment the sample comprises a fluid, such as for example, blood, plasma, saliva etc.

The sample may comprise cells including, but not limited to blood cells, bone marrow cells, pancreatic cells, lung cells, hepatic cells, spleen cells, kidney cells, cardiac cells, ovarian cells, breast tissue cells, skin cells (e.g., epithelial cells, fibroblasts, keratinocytes), lymph node cells. According to a particular embodiment the cells comprise cancer cells. Such cells can be obtained using methods known in the art, including, but not limited to, fine needle biopsy, needle biopsy, core needle biopsy and surgical biopsy (e.g., brain or liver biopsy), buccal smear and lavage.

ErbB ligand amount and/or activity can then be detected in the sample using any structural, biological or biochemical method which is known in the art for detecting the expression level of the RNA encoding the ErbB ligand (using e.g., Northern Blot analysis, RT-PCR analysis, RNA in situ hybridization stain, In situ RT-PCR stain) or the ErbB ligand protein itself (using e.g., Western blot, Enzyme linked immunosorbent assay (ELISA), Radio-immunoassay (RIA), Fluorescence activated cell sorting (FACS), Immunohistochemical analysis).

The amount or activity or the ErbB ligand is then compared to the amount or activity or the ErbB ligand in a control sample. If the amount or activity of the ErbB ligand in the test sample is increased (e.g. at least 1.5 fold, at least 2 fold, at least 5 fold) compared to the control sample, then that ligand may be selected as a target for treatment.

Control samples to which the subject's samples are compared may be obtained from healthy individuals typically of the same species, age and from the same sub-population (e.g. smoker/nonsmoker). Alternatively, the control sample may be derived from the patient himself, but from a non-hyperproliferative tissue (e.g. non-cancerous tissue). Alternatively, control data may be taken from databases and literature.

Once a suitable target is selected, treating may be effected using any agent which down-regulates its amount and/or activity.

As used herein, the term "down-regulating" when relating to the amount and/or activity of the target refers to preventing, reducing, inhibiting, decreasing and/or eliminating the amount and/or activity of an ErbB ligand. According to one embodiment, the decreasing is effected so that the levels are not substantially elevated compared to the control sample. According to another embodiment, the levels are decreased maximally so as to completely eliminate the activity of the ErbB ligand.

A number of agents can be used in accordance with this aspect of the present invention to reduce/down-regulate the amount and/or activity of an ErbB ligand in the hyperproliferative cell (e.g. cancer cell).

Thus, for example, decreasing the expression level of the ErbB ligand can be effected on the genomic and/or the transcript level using a variety of molecules which interfere with transcription and/or translation (e.g., antisense, siRNA, Ribozyme, DNAzyme), or on the protein level using e.g., antagonists, antibodies, enzymes that cleave the polypeptide or inhibit functionality of the peptide and the like.

Following is a list of agents capable of decreasing the amount and/or activity of the ErbB ligand of the present invention.

One example of an agent capable of down-regulating (or decreasing the expression level of) the ErbB ligand of the present invention is an antibody or antibody fragment capable of specifically binding to the ErbB ligand. Preferably, the antibody specifically binds at least one epitope of the ErbB ligand (e.g., EGF-like domain of ErbB ligand). According to one embodiment the antibody has at least a 2 fold higher affinity for a particular ErbB ligand as opposed to any other ErbB ligand. According to one embodiment the antibody has at least a 5 fold higher affinity for a particular ErbB ligand as opposed to any other ErbB ligand. According to one embodiment the antibody has at least a 10 fold higher affinity for a particular ErbB ligand as opposed to any other ErbB ligand.

According to another preferred embodiment of this aspect of the present invention, the antibodies bind their target ErbB ligands with a minimal affinity of at least 1 µM, 200 nM, 100 nM, 1 nM or higher.

Antibodies of this aspect of the present invention can be selected from pre-existing antibodies (e.g., publicly available hybridomas or commercially available antibodies) or from newly generated antibodies produced according to methods which are well-known in the art and further described hereinbelow. Examples of commercially available antibodies include EGF monoclonal antibodies (e.g. Clone S-21 from Abazyme), HB-EGF monoclonal antibodies (e.g. Clone 125923 and Clone 406316 from R&D systems) and TGFα monoclonal antibodies (e.g. Clone 134A-2B3 and Clone 189-2130.1 from Abcam).

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics. The term "antibody" as used in this invention includes intact molecules as well as functional fragments thereof, such as Fab, F(ab')2, Fv or single domain molecules such as VH and VL to an epitope of an antigen. These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference and the Examples section which follows).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that targeting of particular compartment within the cell can be achieved using intracellular antibodies (also known as "intrabodies"). These are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For mitochondrial expression of the light and heavy chains, the nucleotide sequences encoding the mitochondrial targeting sequences are added [e.g., the COOH-terminal signal anchor of Bcl-2 (Nguyen, M. et al., 1993. J. Biol. Chem. 268:25265-25268)]. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker and expressed as a single chain molecule. To inhibit marker activity in a cell, the expression vector encoding the intracellular antibody is introduced into the cell by standard transfection methods, as discussed hereinbefore.

It will be appreciated that once the CDRs of an antibody are identified, using conventional genetic engineering techniques can be used to devise expressible polynucleotides encoding any of the forms or fragments of antibodies described herein.

Also contemplated are bi-epiptopic antibodies, wherein a single antibody is capable of recognizing two ErB ligands. Methods of producing such antibodies are disclosed in US application 2007178102, incorporated herein by reference.

As shown in detail in the Examples section which follows (see e.g. Examples 3 and 4), the present inventors have generated antibodies which specifically target TGFα (designated mAb-551) and HB-EGF (designated mAb-898, mAb-878 and mAb-384). Furthermore, the present inventors have shown that in vivo treatment of mice with these antibodies reduces tumor volume.

Thus, according to an embodiment of the present invention, there is provided a monoclonal antibody or fragment thereof capable of specifically binding to at least one epitope of an EGF-like domain of TGFα as described by deposit number CNCM I-4292 (Clone No. 551.6.103), deposited on Apr. 9, 2010 at the Collection Nationale De Cultures De Microorganismes (CNCM), Institut Pasteur, 25 Rue du Docteur Roux, 75724 Paris Cedex 15.

Thus, according to another embodiment of the present invention, there is provided a monoclonal antibody or fragment thereof capable of specifically binding to at least one epitope of an EGF-like domain of HB-EGF as described by deposit number CNCM I-4291 (Clone No. 898.47), deposited on Apr. 9, 2010 at the Collection Nationale De Cultures De Microorganismes (CNCM).

Another agent capable of downregulating the ErbB ligand of the present invention is a small interfering RNA (siRNA) molecule. RNA interference is a two step process. In the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the mRNA sequence encoding the ErbB ligand (e.g., epidermal growth factor (EGF), GenBank Accession No. NM_001963) is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (www(dot)ncbi (dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

The selected siRNAs can be chemically synthesized oligonucleotides (using e.g., solid phase synthesis) or can be encoded from plasmids in order to induce RNAi in cells following transfection (using e.g., the pRETRO-SUPER vector). Recently, retrovirus- or lentivirus-delivered RNAi were developed and were found efficient in long-term gene silencing in vivo [Hao D L., et al., 2005, Acta. Biochim. Biophys. Sin. (Shanghai), 37(11): 779-83].

For example, a suitable ErbB ligand siRNA can be the EGF siRNA (e.g. sc-39416, Santa Cruz Biotechnology, Inc.) or TGFα siRNA (e.g. sc-39423, Santa Cruz Biotechnology, Inc.) or HB-EGF siRNA (sc-39420, Santa Cruz Biotechnology, Inc.).

Another agent capable of downregulating the ErbB ligand of the present invention is a DNAzyme molecule capable of specifically cleaving an mRNA transcript or DNA sequence of the ErbB ligand. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www(dot)asgt(dot)org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of the ErbB ligand of the present invention can also be effected by using an antisense polynucleotide capable of specifically hybridizing with an mRNA transcript encoding the ErbB ligand (e.g., epidermal growth factor).

Design of antisense molecules which can be used to efficiently down-regulate the ErbB ligand must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for down-regulating expression of known sequences without having to resort to undue trial and error experimentation.

Another agent capable of down-regulating the expression of the ErbB ligand is a ribozyme molecule capable of specifically cleaving an mRNA transcript encoding the ErbB ligand (e.g., EGF, TGFα). Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent which can be used to down-regulate the expression level of the ErbB ligand of the present invention in cells is a triplex forming oligonucleotide (TFO). to Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989, 245:725-730; Moser, H. E., et al., Science, 1987, 238:645-630; Beal, P. A., et al, Science, 1992, 251:1360-1363; Cooney, M., et al., Science, 1988, 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
|---|---|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, 3: 27). The same authors have demonstrated that TFOs designed according to the A-AT and G-GC rule do not form non-specific triplexes, indicating that the triplex formation is indeed sequence specific.

Thus for any given sequence in the ErbB ligand regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFGl and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

According to the present teachings, and as shown in detail in Examples 5 and 6 of the Examples section which follows, co-administration of two agents (e.g. antibodies) each targeting a different ErbB ligand (e.g. first ErbB ligand and a second ErbB ligand) to the subject efficiently eradicate tumor cell growth.

Thus, according to another aspect of the present invention, a hyperproliferative disease may be treated via the administration of two agents, for example, two antibodies or two siRNA molecules each targeting a non-identical ErbB ligand, one antibody and one siRNA molecule each targeting a non-identical ErbB ligand. Administration of the two agents may be carried out concomitantly or subsequent to each other.

The present invention envisions the use of more than two agents to down-regulate ErbB ligands. The number of targets (as well as the identity thereof) is typically determined during the analysis phase of the procedure.

In addition, the present invention may be used along with agents which down-regulate an ErbB receptor, such as blocking antibodies, small kinase inhibitors and soluble ligand receptor traps/decoys [described in detail in Cardó-Vila et al. (2010) PNAS 107(11) 5118-5123, fully incorporated herein by reference].

It will be appreciated that the agent of the present invention (e.g., the antibody, siRNA, or an expression vector encoding same) can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent (e.g. antibody, siRNA) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (i.e. agent e.g. antibody or siRNA) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and administration intervals may be adjusted individually to provide sufficient plasma or tissue levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. The dosage and timing of administration will be responsive to a careful and continuous monitoring of the individual changing condition.

Models for cancer include, but are not limited to, murine animal models including NCr-nude mice inoculated with MiaPaCa human pancreatic cancer cells (i.e. pancreatic cancer animal model) or with the human lung tumor cell line H1437 (i.e. lung cancer animal model).

Regardless of the above the agents of the present invention are administered at an amount selected to avoid unwanted side-effects (e.g., up-regulated immune response).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The ErbB ligand down-regulating agents of the present invention can be suitably formulated as pharmaceutical compositions which can be packaged as an article of manufacture. Such an article of manufacture comprises a label for use in treating a hyperproliferative disease, the packaging material packaging a pharmaceutically effective amount of the agents (i.e. a first agent which down-regulates a first ErbB ligand and a second agent which down-regulates a second ErbB ligand). It will be appreciated that the agents of the present invention may be formulated in separate pharmaceutical compositions or alternatively may be formulated in a single pharmaceutical composition.

In order to enhance treatment of the hyperproliferative disease, the present invention further envisions administering to the subject an additional therapy such as radiotherapy or chemotherapy. Analgesic agents and other treatment regimens are also contemplated. Examples of chemotherapeutic agents include, for example, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

Such a chemotherapy agent (e.g., gemcitabine) can also be conjugated to the antibody of the present invention.

In addition, to increase the specific biological activity exerted by the antibody of the present invention such an antibody can further include a cytotoxic agent (i.e., a drug) such as Pseudomonas exotoxins PE35, PE38, PE40, Pseudomonas aeroginosa exotoxin A (ETA'), and diphtheria toxin (DT390), to thereby form a specific immunotoxin. Such a cytotoxic agent can be attached to the antibody.

The antibodies taught by the present invention may be further used for detection of an ErbB ligand in a hyperproliferative cell or tissue (e.g. cancer cell or tissue), or for assessment of down-regulation of same. For diagnostic applications, antibodies typically will be labeled with a detectable moiety. The detectable moiety can be any one which is capable of producing, either directly or indirectly, a detectable signal. For example, the detectable moiety may be a radioisotope, a fluorescent or chemiluminescent compound, or a tag (such as described hereinabove and to which a labeled antibody can bind). The antibodies of the present invention may be employed in any known assay method, such as competitive binding assays, direct and indirect sandwich assays, and immunoprecipitation assays. [Zola, Monoclonal Antibodies: A Manual of Techniques, pp. 147-158 (CRC Press, Inc., 1987)].

The antibodies of this aspect of the present invention can be included in a diagnostic kit, in which the antibodies and optionally solid support and imaging reagents (e.g., antibodies, chromogenic substrate etc.) can be packaged in suitable containers with appropriate buffers and preservatives and used for diagnosis.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Secretion of EGF-Like Ligands from Tumor Cell Lines

Materials and Experimental Procedures

Materials

Growth factors were purchased from PeproTech Asia (Peprotech, Rocky Hill, N.J.). NiNTA beads were purchased from Novagen (Madison, Wis.). Beads conjugated to anti-mouse Fc antibodies, ATBS (2,2'-Azino-bis(3-ethylbenzthiozoline-6-sulfonic acid) and MTT (3-(4,5-Dimethylthiazol-2-yl)-2,5-diphenyltetrazolium bromide) were purchased from Sigma (Sigma, St. Louis, Mo.). Duo-set kits for growth factor assays were purchased from R&D Systems (R&D Systems, Minneapolis, Minn.). Hygromycin was purchased from Invitrogen (Carlsbad, Calif.). Gemcitabine was purchased from Eli Lilly LTD. (Eli Lilly LTD., Hampshire, England). Monoclonal antibodies to EGFR and ErbB-3 were generated as described herein.

An antibody to phosphotyrosine (p-Tyr) was purchased from Santa-Cruz (Santa Cruz, Calif.). Horseradish peroxidase (HRP)-conjugated anti-mouse antibody was purchased from Jackson Immuno Research Laboratories (West Grove, Pa.).

Cell Lines and Tissue Culture

HeLa, T47D, NSO and MiaPaCa were cultured in DMEM medium. BxPC3 cells were cultured in RPMI medium. Chinese hamster ovary (CHO) cells were maintained in a mixture of Dulbecco's modified Eagle's medium (DMEM) and F12 (1:1). All media were supplemented with 10% heat-inactivated fetal calf serum.

Determination of Ligand Concentrations in Conditioned Medium

Human cancer cell lines ($1 \times 10^6$) were seeded in 10-cm plates, covered with 8 ml medium and incubated for four days. Media were then collected and ligand quantified using the DuoSet ELISA kit following the manufacturer's instructions (R&D Systems, Minneapolis, Minn.).

Results

Inventors examined the secretion of different EGF-like ligands from tumor cell lines. For this purpose, inventors used an immunological kit able to detect low concentrations of four different ligands of EGFR, namely EGF, TGFα, HB-EGF and AR. The assay was performed on media conditioned by 13 carcinoma cell lines derived from a wide variety of human tumors such as ovary, breast, lung and pancreas (Table 1, below). As depicted in detail in Table 1, the assay detected distinct combinations of growth factors, with HB-EGF and AR being the most abundant ligands secreted by the tumor cell lines tested.

TABLE 1

In-vitro secretion of EGF-like ligands by human cancer cell lines

| cell line | Tumor type | TGFα | EGF | HB-EGF | AR |
|---|---|---|---|---|---|
| MDA-MB-231 | breast | 111.9 ± 1.0 | — | 616.7 ± 27.9 | 1606.9 ± 171.1 |
| MDA-MB-468 | breast | — | — | 63.6 ± 6.6 | — |
| SKBR3 | breast | — | 4.8 ± 1.0 | — | 34.4 ± 6.2 |
| A-431 | epidermoid | 12.8 ± 2.5 | — | 222.7 ± 9.5 | 81.9 ± 17.8 |
| H1437 | lung | 27.0 ± 2.6 | — | 60.9 ± 27.0 | 2121.4 ± 84.7 |
| OVCAR3 | ovary | 13.2 ± 10.4 | — | 104.9 ± 33.7 | 276.2 ± 21.0 |
| SKOV3 | ovary | — | — | — | 28.1 ± 12.4 |
| TOV112 | ovary | — | — | 83.4 ± 4.2 | — |
| BxPC3 | pancreas | 21.4 ± 0.2 | — | 213.1 ± 62.0 | 3305.5 ± 49.6 |
| MiaPaCa | pancreas | — | — | 133.7 ± 42.2 | 3794.2 ± 15.2 |
| PANC-1 | pancreas | — | — | 147.7 ± 31.7 | 200.8 ± 12.7 |
| DU145 | prostate | 26.1 ± 2.6 | — | 126.9 ± 25.6 | 2574.7 ± 198.7 |
| PC3 | prostate | 14.2 ± 9.5 | 2.9 ± 2.1 | 324.6 ± 53.5 | 3822.4 ± 33.0 |

Example 2

Cloning, Expression and Biological Activity of EGF-Like Ligands

Materials and Experimental Procedures

Materials

As described in detail in Example 1, hereinabove.

Cloning and Expression of EGF-Like Ligands in Bacteria and in Mammalian Cells

The EGF-like domains of TGFα (SEQ ID NO: 1) or HB-EGF (SEQ ID NO: 3) were cloned into the pET32b vector, and expressed as a C-terminal thioredoxin (TRX) fusion protein with a Factor Xa cleavage site flanking to the N-terminal residue of the EGF-like domain. The resultant fusion proteins were expressed in *Escherichia coli* (BL21) using standard procedures. One colony was grown overnight, and diluted into 200 ml 2YT. OD (600 nm) was monitored continuously until reaching 0.5-0.6, then 1 mM IPTG was added and the culture was moved to 30° C. Following 5 hours of incubation, bacterial cells were cooled on ice, centrifuged and re-suspended in a mixture containing 20 ml of 20 mM Tris pH-7.5, 150 mM NaCl, 5 mM immidazole and 1% triton X-100. Cells were then broken by sonication, and cleared extracts were transferred to pre-equilibrated NiNTA beads. The beads were washed using the same buffer, and eluted with 300 mM immidazole.

Construction of fusion proteins comprising an EGF-like domain linked to a GPI attachment motif was performed in two steps. The first PCR reaction was performed on the GPI signal of the rat contactin-1. The 5' primer introduced a NsiI cleavage site which was followed by an HA tag, and the 3' primer introduced a NotI site. The product was cloned into the pIRES-Hyg vector using the NsiI and NotI restriction enzymes. The second step employed overlapping PCR. The first reaction used the signal peptide of HER2 as a template, and a 3' primer that included the 5' sequence of the respective EGF-like domain. The second PCR reaction used the respective EGF-like domain as a template, and a 5' primer which included the 3' end of the HER2 signal peptide. The products of both reactions were purified, and combined in a molar ratio of 1:1, which served as a template for another PCR reaction. The final PCR product was cloned into pIRES-Hyg-GPI inframe and 5' to the HA tag by using BamHI and NsiI cleavage sites.

Immunoblot Analyses

Cells were seeded in a 24-well plate. Twenty-four hours later, cells were washed and incubated with different agents. After ten minutes of incubation, the cells were lysed and cleared extracts were electrophoresed, then immunoblotted with an anti-phosphotyrosine mAb, an anti-EGFR mAb (HeLa) or with an anti-ErbB-3 mAb (T47D).

Results

Figure 1A:
FIGS. 1A-E depict construction, expression and biological activity of recombinant EGF-like ligands and detection of TGFα blocking antibodies using a GPI-anchored TGFα.
Figure 1B:
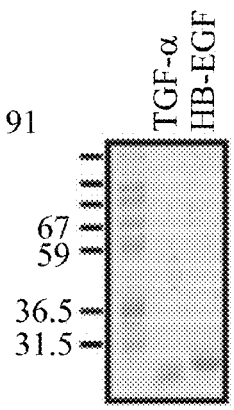
Figure 1C:
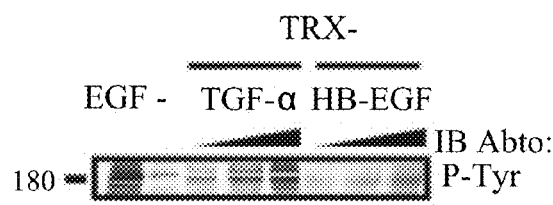

Specific recognition and binding to the native conformation of the target are the hallmarks of monoclonal antibody (mAbs)-based therapy. It is known that highly conserved three disulfide bonds are responsible for the correct folding and activity of the EGF-like domain of all ErbB ligands [Van Zoelen, E. J., et al. (2000) Vitam Horm 59, 99-131]. Therefore, inventors chose to express the EGF-like domain of EGFR-specific ligands as fusion proteins, linked to the thioredoxin protein (TRX, FIG. 1A). The fused protein also contained a histidine repeat that enables subsequent purification by the use of a Nickel column (e.g. NiNTA column). In addition, a factor Xa cleavage site was introduced to enable the release of the EGF-like domain from the rest of the recombinant protein. Following expression in a bacterial system (as described in detail in the materials and methods section above), two ligands (TGFα and HB-EGF) were purified using a NiNTA column (FIG. 1B) and their biological activity was verified by testing their ability to induce EGFR phosphorylation on tyrosine residues (FIG. 1C). As shown in FIG. 1C, the recombinant ligands represented the respective functionally active conformation. Hence, mice were subsequently immunized with the active TRX-fused ligands as detailed hereinbelow and in the materials and methods section (hereinbelow).

Example 3

Generation of an Antagonistic Antibody Directed Against the EGF-Like Domain of TGFα

Materials and Experimental Procedures

Materials

As described in detail in Example 1, hereinabove.

Cloning and Expression of EGF-Like Ligands in Bacteria and in Mammalian Cells

As described in detail in Example 2, hereinabove.

Expression of EGF-Like Ligands in Mammalian Cells

To establish clones of Chinese hamster ovary (CHO) cells stably expressing an EGF-like domain inventors transfected the corresponding pIERS-Hyg using Lipofectamine (Invitrogen, Carlsbad, Calif.), and selected clones using hygromycin (2 µg/ml). Following two weeks of selection, stably transfected cells appeared as small colonies, which were screened and the colonies with high expression were propagated.

Generation of Monoclonal Antibodies

Five Female balb/c mice (3 month old; Harlen, Israel) were injected subcutaneously and intra foot pad of one leg, with 30 µg protein in complete Freund's adjuvant. Three weeks later, a second injection was carried out in incomplete Freund's adjuvant. This injection was followed by 3-5 injections of 30 µg protein in PBS at intervals of 3 weeks. Ten days after the last injection the mice were bled and the serum was tested for antibodies titer. A month after the last boost, the two mice with the highest titer received two more injections on two consecutive days. Four days after the last boost, spleens were removed and cells from each individual spleen were fused with 20×10$^6$ NS0/1 myeloma line. Fusion was carried out using 41% polyethylene glycol 1500 (Serva, Heidelberg, GMBH) as was previously described [Eshhar, Z., et al. (1980). J Immunol 124, 775-780]. Following fusion, cells were distributed into 96-well plates, at concentration of 2×10$^4$ viable myloma cells/well. Hybrid cells were selected for growth in the presence of HAT. Positive hybrid cultures were weaned out of HAT, cloned and recloned in limiting dilution.

In Vitro Testing of mAb Binding to EGF-Like Ligands 96 well plates were coated with the indicated ligands (at 0.1 ng/ml) and incubated for 3 hours at 37° C. Plates were washed twice and blocked with 1% BSA in PBST for 1 hour in 37° C., followed by 3 hours incubation at room temperature with an antibody (1 µg/ml) or with saline. Wells were then incubated for 20 minute with an anti-mouse HRP antibody, followed by incubation with the ATBS (Sigma, St. Louis, Mo.) reagent. Signals were determined using an ELISA reader (420 nm).

Immunoprecipitation Assays mAbs were incubated with agarose beads conjugated to anti-mouse Fc antibodies for 45 min. Thereafter, the beads were washed twice in PBS and incubated with HB-EGF or TGFα (Sigma, St. Louis, Mo.) for 1 hour. Immune complexes were immunoblotted with mAb327 to HB-EGF.

Results

Figure 1E:
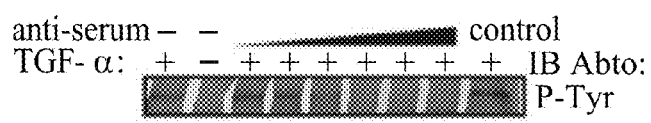
Figure 1D:
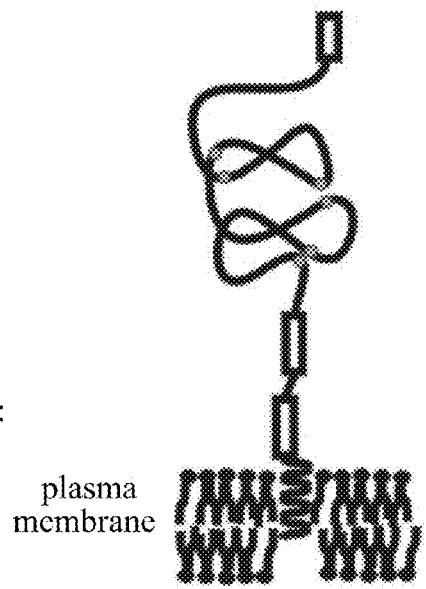

TRX-containing fusion proteins were used to immunize Balb/c mice (50 µg per animal), using complete Freund's adjuvant (Tifco, Detroit, Mich.). Following four intraperitoneal injections, sera were obtained and examined for anti-ligand response. To facilitate anti-serum and hybridoma screening, inventors established a stable Chinese hamster ovary (CHO) cell line that expressed the EGF-like domain of TGFα on the plasma membrane. The EGF-like domain was fused to the HER2 signal peptide, an HA-peptide tag and a GPI-anchor (glycosyl phosphatidylinositol) motif, which is responsible for lipid-based anchoring of the fusion protein on the plasma membrane (FIG. 1D). Antisera derived from immunized mice were tested for their ability to specifically bind CHO cells expressing the GPI-anchored ligand. In addition, inventors tested the ability of antisera to inhibit ligand-induced EGFR phosphorylation. As shown in FIG. 1E (an example assay), TGFα-induced phosphorylation of EGFR was tested in the presence of increased amounts of antisera from an immunized mouse. Subsequently, the spleens of two positive mice were used to establish hybridomas, which were then screened for their ability to recognize surface-exposed GPI-TGFα fusion protein and also to pull-down the mammalian recombinant ligand (data not shown).

Figure 2B:
Figure 2C:
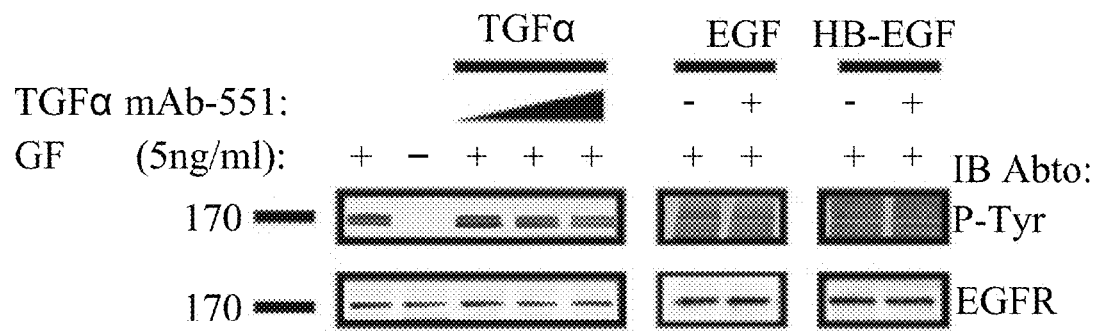

To functionally characterize a selected anti-TGFα mAb, denoted mAb-551, inventors tested its specificity using an ELISA assay. This assay confirmed that mAb 551 bound only to TGF-α and not to the other four ligands tested (AR, EGF, HB-EGF and NRG1, FIG. 2A). Further, the anti-TGFα mAb was found to immunopercipitate a commercial preparation of TGFα (FIG. 2B). Moreover, inventors confirmed the ability of mAb-551 to specifically inhibit TGFα-induced EGFR phosphorylation (FIG. 2C) while neither EGF- nor HB-EGF-induced activation of EGFR were inhibited (FIG. 2C). Taken together, these results established suitability of mAb-551 to intercept TGFα-mediated autocrine loops.

Example 4

Figure 3B:
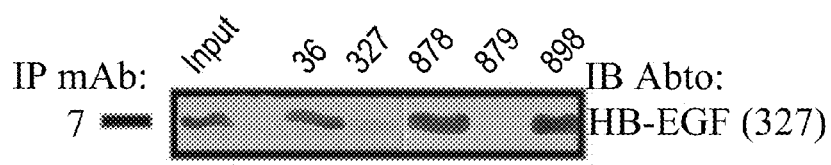
Figure 3C:
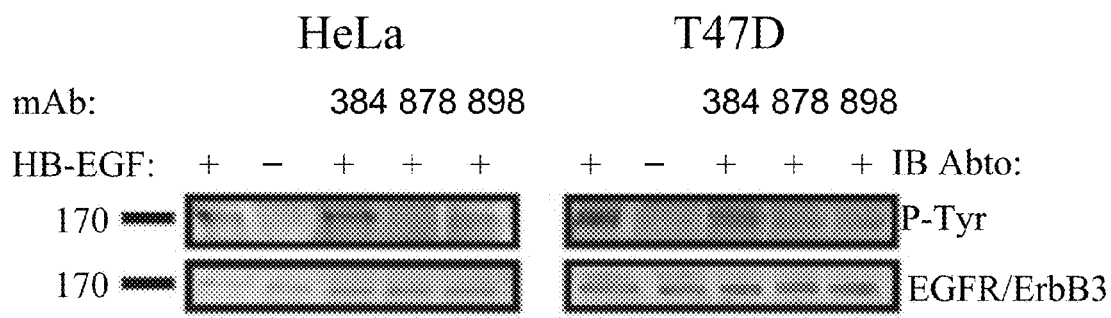

Generation of an Antagonistic Antibody Directed Against the EGF-Like Domain of HB-EGF Materials and Experimental Procedures
Materials
As described in detail in Example 1, hereinabove.
Cloning and Expression of EGF-Like Ligands in Bacteria and in Mammalian Cells
As described in detail in Example 2, hereinabove.
Expression of EGF-Like Ligands in Mammalian Cells
As described in detail in Example 3, hereinabove.
Generation of Monoclonal Antibodies
As described in detail in Example 3, hereinabove.
In Vitro Testing of mAb Binding to EGF-Like Ligands
As described in detail in Example 3, hereinabove.
Immunoprecipitation Assays
As described in detail in Example 3, hereinabove.
Results Inventors generated mAbs to another major growth-stimulating EGF-like ligand, HB-EGF. Using three mAbs to HB-EGF and an immobilized HB-EGF, inventors confirmed specificity and absence of cross-reactivity toward other growth factors of the ErbB family (FIG. 3A). Next, inventors confirmed the ability of three positive clones of hybridomas to immunoprecipitate a commercial preparation of HB-EGF (FIG. 3B). In addition, by testing HB-EGF-induced tyrosine phosphorylation in HeLa and in T47D mammary cancer cells, inventors concluded that the three mAbs to HB-EGF (mAb-898, mAb-878 and mAb-384) variably inhibited ligand-induced receptor activation (FIG. 3C).

Example 5

Growth-Inhibitory Activities of Individual Antibodies and their Combination

Materials and Experimental Procedures
Materials
As described in detail in Example 1, hereinabove.
Cloning and Expression of EGF-Like Ligands in Bacteria and in Mammalian Cells
As described in detail in Example 2, hereinabove.
Generation of Monoclonal Antibodies
As described in detail in Example 3, hereinabove.
Cell Proliferation Assay (MTT)

BxPC3 pancreatic tumor cells were plated on 96-well plates (2,000 cells/well), in hexaplicates. The cells were allowed to adhere overnight prior to the addition of different mAbs. Proliferation was measured after 24, 48 and 72 hours using the MTT method as was previously described [Mossmann T. J., Immunol Methods. (1983) 16; 65 (1-2):55-63]. MTT (3-(4,5-D imethylthi azol-2-yl)-2,5-diphenyltetrazolium bromide) was added to the wells and two hours later the cells were dissolved in 4 mM HCl (in isopropanol). Absorbance was determined at 570 nm.

Determination of Anti-Tumor Activity of mAbs in Animals

Female atymic NCr-nude mice (6 week old; Harlen, Israel) were inoculated subcutaneously with $2\times10^6$ human cancer cells. Once tumors became palpable (5-7 days), mice were randomized into groups and injected intraperitoneally at the indicated time points, with a mAb, chemotherapy or various combinations. Tumor volumes were monitored twice a week, and body weights were measured once a week.

Results

Combination therapy often proves to be more efficient than mono-therapy. The availability of antagonistic mAbs to TGFα and to HB-EGF, along with the finding that BxPC3 pancreatic tumor cells secreted both ligands (Table 1, hereinabove), prompted inventors to test combined treatment targeting two autocrine growth factors on tumorigenic growth of BxPC3 cells. To this end, inventors quantified proliferation of BxPC3 cells in the presence of each of the mAb generated, or a combination of the two antibodies. The results (presented in FIG. 4A) demonstrated an inhibitory effect of both mAb-551 (to TGFα) and mAb-898 (to HB-EGF) on cell proliferation. Importantly, a combined treatment with both mAbs increased the inhibitory effect on BxPC3 cell proliferation, consistent with simultaneous autocrine loops.

Inventors further checked the in vivo efficacy of combining two anti-growth factor mAbs using the same pancreatic BxPC3 xenografts. Cells were injected subcutaneously into mice (as described in the materials and methods section above) and were allowed to grow until palpable tumors appeared (5-7 days). The mice were then treated twice a week with one of the mAb (mAb-551 or mAb-898) or with the combination of anti-TGFα and anti-HB-EGF mAbs (FIG. 4B). As shown in FIG. 4B, not only did the in vivo activity of these mAbs appear to be more profound than the in vitro results, the combination of the two mAbs led to a synergistic effect, with a reduction in tumor size which was greater than the reduction observed with each of the mAbs separately. Monitoring the body weight of the mice revealed no consistent effect of the mAbs or combinations of same (data not shown). In addition, inventors found that xenografts of the pancreatic cell line MiaPaCa-2 and the lung cancer cell line H1437 were better inhibited by a combination of the two mAbs rather than by individual treatments with either mAb-551 or mAb-898 (data not shown). Thus, combining antibodies to two growth factors appeared to induce a broad growth-inhibitory effect without toxicity.

Example 6

A Combination of Anti-Growth Factor Antibodies Sensitizes Tumors to Chemotherapy Materials and Experimental Procedures
Materials
As described in detail in Example 1, hereinabove.
Cloning and Expression of EGF-Like Ligands in Bacteria and in Mammalian Cells
As described in detail in Example 2, hereinabove.
Generation of Monoclonal Antibodies
As described in detail in Example 3, hereinabove.

Cell Proliferation Assay (MTT)

BxPC3 pancreatic tumor cells were plated on 96-well plates (2,000 cells/well), in hexaplicates. The cells were allowed to adhere overnight prior to the addition of the two mAbs mAb-551 or mAb-898 or gemcitabine. Proliferation was measured after 24, 48 and 72 hours using the MTT method. MTT (3-(4,5-Dimethylthiazol-2-yl)-2,5-diphenyltetrazolium bromide) was added to the wells and two hours later the cells were dissolved in 4 mM HCl (in isopropanol). Absorbance was determined at 570 nm.

Determination of Anti-Tumor Activity of mAbs in Animals

Female atymic NCr-nude mice (6 week old; Harlen, Israel) were inoculated subcutaneously with $2\times10^6$ human cancer cells. Once tumors became palpable (5-7 days), mice were randomized into groups and the mice were treated (by intraperitoneal injections) twice (on days 16 and 21) with gemcitabine (150 mg/kg body weight) and twice a week with or without the two mAbs. Tumor volumes were monitored twice a week, and body weights were measured once a week.

Results

Figure 5A:
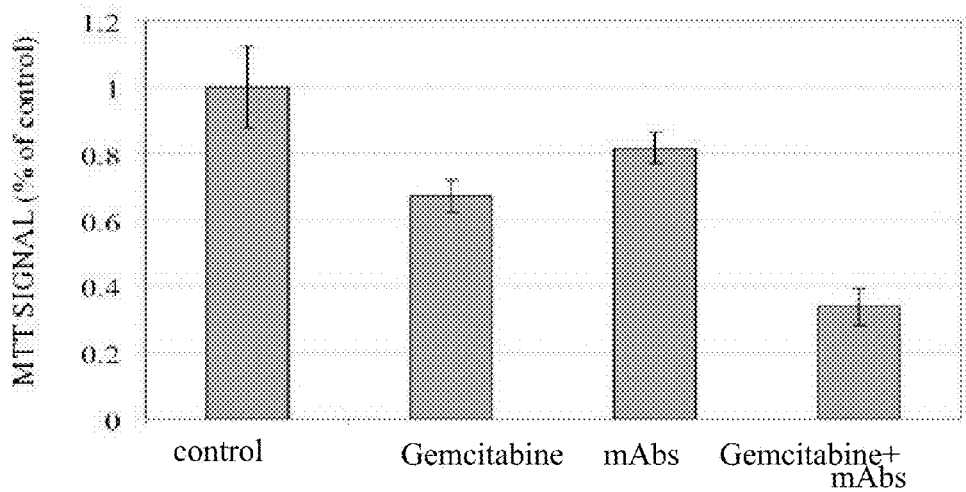
FIGS. 5A-B depict effective inhibition of human pancreatic cancer cell growth (in vitro and in vivo) by a combination of two mAbs and chemotherapy.
Figure 5B:
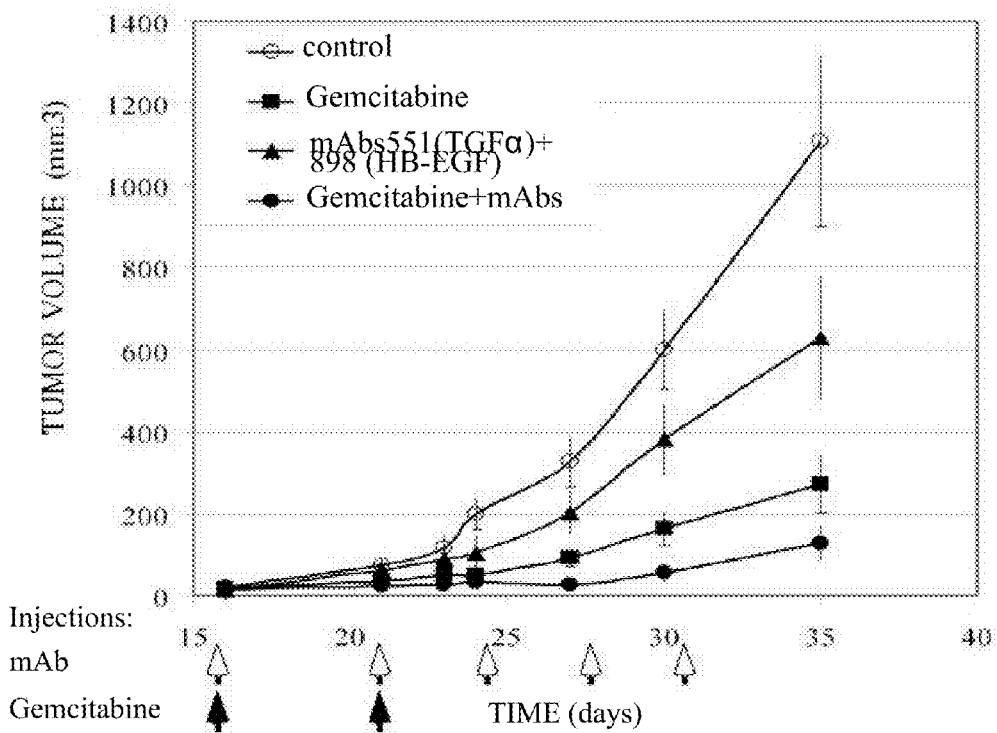
Figure 6A:
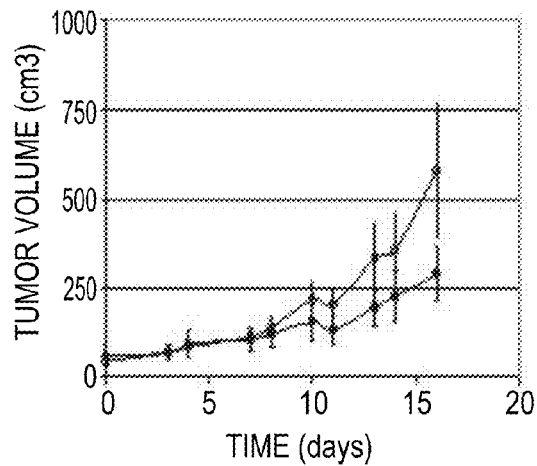
FIGS. 6A-D depict inhibition of human tumor cell growth in an animal model by anti-TGFα and anti-HB-EGF mAbs. Nude mice bearing palpable tumors of MiaPaCa human pancreatic cancer cells (FIGS. 6A and 6C) or human lung tumor cell line H1437 (FIGS. 6B and 6D) were treated with a combination of anti-TGFα and anti-HB-EGF mAbs twice a week (125 μg each). Mice bearing MiaPaCa xerografts were treated on days 14, 18, 21, 24, 27, 30, 34 and 37 with the mAbs. The control group comprised 8 mice and the treatment group comprised 5 mice. Mice bearing H1437 tumor xenografts were treated on days 6, 10, 14, 17 and 21 with the mAbs. The corresponding control group comprised 15 mice and the treatment group comprised 11 mice (FIG. 6B). Tumor volume (FIGS. 6A-B) and body weight (FIGS. 6C-D) are shown. Black circles represent mice treated with mAbs (anti-TGFα and anti-HB-EGF) and white circles represent control mice.
Figure 6C:
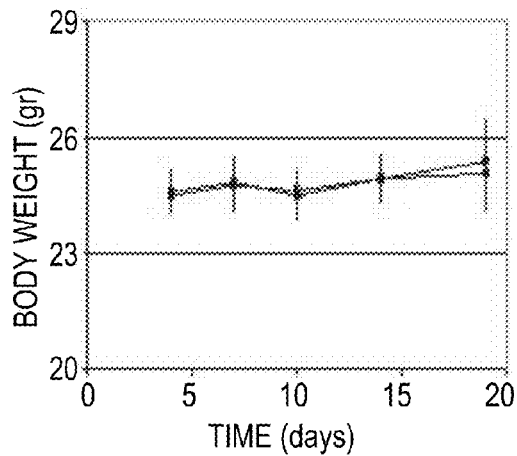
Figure 6B:
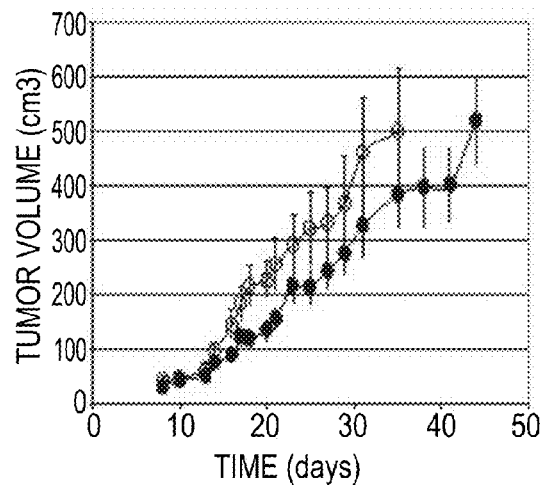
Figure 6D:
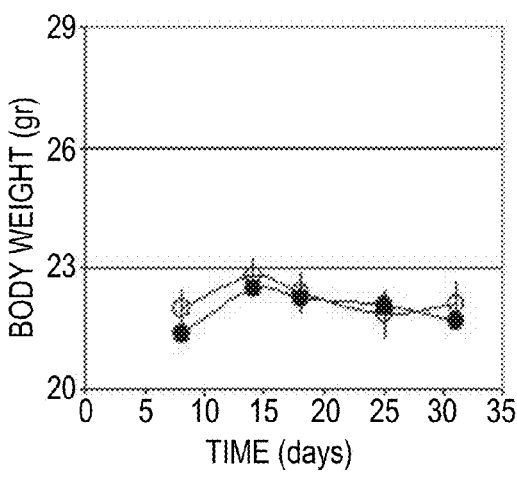

The inventors of the present invention assume that self-produced growth factors that stimulate EGFR (ErbB-1) and HER2 (ErbB-2), along with ErbB-3/4, play an essential role in resistance of pancreatic and other tumors to chemo- and radiotherapy. Hence, the present inventors wanted to test whether blocking such autocrine loops would shut-down escape mechanisms and re-sensitize tumors to the toxic effects of conventional therapies. As an initial test of this scenario, inventors examined in vitro the combined effect of two mAbs and gemcitabine, the mainstay chemotherapeutic drug of advanced pancreatic tumors. As shown in FIG. 5A, using the mixture of antibodies to TGFα and HB-EGF (mAb 551 and mAb 898, respectively) augmented the growth inhibitory effect of gemcitabine (as seen on cultured BxPC3 cells).

In the next experiment, inventors examined in animals the effect of a triple combination, namely gemcitabine, mAb 551 and mAb 898, on the tumorigenic growth of BxPC3 cells. Cells were injected subcutaneously and allowed to grow until palpable tumors appeared. The mice were then treated twice (days 16 and 21) with gemcitabine (150 mg/kg body weight) and with or without the two mAbs. The results presented in FIG. 5B demonstrated that two injections of gemcitabine resulted in more than 85% inhibition of tumor growth, however, repeated injections with a mixture of the two mAbs augmented the cytotoxic effect of this chemotherapeutic agent.

Example 7

A Combination of Anti-Growth Factor Antibodies Significantly Reduce Pancreatic and Lung Tumors In Vivo Materials and Experimental Procedures
Materials
As described in detail in Example 1, hereinabove.
Cloning and Expression of EGF-Like Ligands in Bacteria and in Mammalian Cells
As described in detail in Example 2, hereinabove.
Generation of Monoclonal Antibodies
As described in detail in Example 3, hereinabove.

Determination of Anti-Tumor Activity of mAbs in Animals

Female atymic NCr-nude mice (6 week old; Harlen, Israel) were inoculated subcutaneously with $2 \times 10^6$ MiaPaCa human pancreatic cancer cells or with the human lung tumor cell line H1437. Once tumors became palpable (5-7 days), mice bearing MiaPaCa xerografts were treated on days 14, 18, 21, 24, 27, 30, 34 and 37 with the mAbs (each at 125 µg per injection). The control group comprised 8 mice and the treatment group comprised 5 mice. Mice bearing H1437 tumor xenografts were treated on days 6, 10, 14, 17 and 21 with the mAbs (each at 125 µg per injection). The corresponding control group comprised 15 mice and the treatment group comprised 11 mice. Tumor volume and mice body weights were monitored.

Results

As shown in FIGS. 6A-D, treatment of mice with anti-TGFα and anti-HB-EGF mAbs significantly reduced pancreatic and lung tumors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or to identification of any reference in this application shall not be construed as an admission that such reference is available as prior art to the present invention. To the extent that section headings are used, they should not be construed as necessarily limiting.

Text File Content

The following lists the content of the text file which is enclosed herewith and filed with the application. File information is provided as: File name/byte size/date of creation/operating system/machine format.

Sequence_Listing/1,869 bytes/18 Apr. 2010/PC/Notepad

What is claimed is:

1. A method of alleviating the progression of an ErbB-family expressing cancer in a subject in need thereof, the method comprising:
   (a) administering a therapeutically effective amount of a first antibody or fragment thereof having the complementarity-determining regions (CDRs) of the monoclonal antibody deposit number CNCM I-4292 (Clone No. 551.6.103), deposited at the Collection Nationale De Cultures De Microorganismes (CNCM); and
   (b) administering a therapeutically effective amount of a second antibody or fragment thereof having the CDRs of the monoclonal antibody deposit number CNCM I-4291 (Clone No. 898.47), deposited at CNCM, thereby alleviating the progression of an ErbB-family expressing cancer in said subject.

2. The method of claim 1, further comprising administering to said subject a chemotherapeutic agent.

3. The method of claim 1, wherein said cancer is a pancreatic cancer.

4. The method of claim 1, wherein said cancer is a lung cancer.

5. The method of claim 1, wherein said cancer is selected from the group consisting of breast cancer, ovarian cancer, epidermoid cancer and prostate cancer.

6. The method of claim 1, wherein said subject is selected having increased levels of TGFα and HB-EGF in a biological sample comprising a fluid and/or cancer cells as compared to a control sample obtained from a healthy subject.

* * * * *

```
SEQUENCE LISTING

<160> NUMBER OF SEQ ID NOS: 4

<210> SEQ ID NO 1
<211> LENGTH: 144
<212> TYPE: DNA
<213> ORGANISM: Homo sapiens

<400> SEQUENCE: 1
tcccatttta atgactgccc agattcccac actcagttct gcttccatgg aacctgcagg      60
tttttggtgc aggaggacaa gccagcatgt gtctgccatt ctgggtacgt tggtgcacgc     120
tgtgagcatg cggacctcct ggcc                                            144

<210> SEQ ID NO 2
<211> LENGTH: 48
<212> TYPE: PRT
<213> ORGANISM: Homo sapiens

<400> SEQUENCE: 2

Ser His Phe Asn Asp Cys Pro Asp Ser His Thr Gln Phe Cys Phe His
1               5                   10                  15

Gly Thr Cys Arg Phe Leu Val Gln Glu Asp Lys Pro Ala Cys Val Cys
            20                  25                  30

His Ser Gly Tyr Val Gly Ala Arg Cys Glu His Ala Asp Leu Leu Ala
        35                  40                  45

<210> SEQ ID NO 3
<211> LENGTH: 48
<212> TYPE: PRT
<213> ORGANISM: Homo sapiens

<400> SEQUENCE: 3

Lys Lys Arg Asp Pro Cys Leu Arg Lys Tyr Lys Asp Phe Cys Ile His
1               5                   10                  15

Gly Glu Cys Lys Tyr Val Lys Glu Leu Arg Ala Pro Ser Cys Ile Cys
            20                  25                  30

His Pro Gly Tyr His Gly Glu Arg Cys His Gly Leu Ser Leu Pro Val
        35                  40                  45
```

```
<210> SEQ ID NO 4
<211> LENGTH: 144
<212> TYPE: DNA
<213> ORGANISM: Homo sapiens

<400> SEQUENCE: 4
aagaagaggg acccatgtct tcggaaatac aaggacttct gcatccatgg agaatgcaaa      60
tatgtgaagg agctccgggc tccctcctgc atctgccacc cgggttacca tggagagagg     120
tgtcatgggc tgagcctccc agtg                                            144
```